US008441634B2

(12) United States Patent
Manian

(10) Patent No.: US 8,441,634 B2
(45) Date of Patent: May 14, 2013

(54) METHODS FOR CALIBRATING A MEASUREMENT DEVICE, AND DEVICES THEREFROM

(75) Inventor: Bala S. Manian, Los Altos Hills, CA (US)

(73) Assignee: Reametrix, Inc., San Carlos, CA (US)

(*) Notice: Subject to any disclaimer, the term of this patent is extended or adjusted under 35 U.S.C. 154(b) by 171 days.

(21) Appl. No.: 13/034,380

(22) Filed: Feb. 24, 2011

(65) Prior Publication Data
US 2012/0105842 A1   May 3, 2012

(51) Int. Cl.
*G01J 3/44* (2006.01)
(52) U.S. Cl.
USPC .......................................................... 356/301
(58) Field of Classification Search .............. 356/72–73, 356/301; 422/69
See application file for complete search history.

(56) References Cited

U.S. PATENT DOCUMENTS

2009/0311798 A1* 12/2009 Wimberger-Friedl et al. ............................ 436/171

OTHER PUBLICATIONS

"Relative Intensity Correction Standards for Fluorescence and Raman Spectroscopy", http://www.nist.gov/mml/biochemical/bioassay/fluorescence_raman_intensity_standards.cfm.
Standard Reference Material 2241, "Relative Intensity Correction Standard for Raman Spectroscopy: 785 nm Excitation", Certificate of Analysis, National Institute of Standards & Technology, Certificate Issue Date: Jun. 27, 2002.
Resch-Genger et al., Fluorescence standards: Classification, terminology, and recommendations on their selection, use and production (IUPAC Technical Report), Pure Appl. Chem., vol. 82, No. 12, pp. 2315-2335, 2010.

* cited by examiner

*Primary Examiner* — Tarifur Chowdhury
*Assistant Examiner* — Abdullahi Nur
(74) *Attorney, Agent, or Firm* — Schneck & Schneck; Thomas Schneck

(57) ABSTRACT

The invention provides a method of calibrating measurement device using a Raman-active composition, wherein the composition is active, in one embodiment, in a wavelength region that ranges from about 300 nm to about 1200 nm, and in another embodiment, from about 550 nm to about 650 nm. The method is especially useful in the calibration of fluorescent measurement devices. The method of the invention provides several advantages, such as, in facile identification of problems with the device when it occurs, in not having to tune and adjust the device very often, and neutralizing variations between different runs and different instruments. In another aspect, the invention also provides a device that is calibrated using the method of the invention. In one embodiment, the Raman-active composition useful in the invention is a derivative of 1,4-bis(2-methyl-styryl)-benzene.

15 Claims, No Drawings

METHODS FOR CALIBRATING A MEASUREMENT DEVICE, AND DEVICES THEREFROM

CROSS REFERENCE TO RELATED APPLICATION

This application claims priority from International Application No. PCT/IB2010/054966, filed on Nov. 3, 2010.

FIELD OF THE INVENTION

The invention relates generally to a method of calibration of a measurement device and more specifically to the use of a Raman-active composition for the calibration of a fluorescence measurement device.

BACKGROUND OF THE INVENTION

Optical measurement devices require accurate aligning of sample towards the optics side of the device and the optical detectors. Any slight deviation from the proper alignment results in erroneous measurement, inaccurate data, and sometimes complete breakdown of the device. Thus, any optical device requires proper positioning and alignment of all the relevant parts of the device, which positioning and alignment has to be maintained throughout the operating life of the device. However, in practical situations, this may not be possible as there is bound to be some shake and movement during use. Hence, there needs to be some manner of determining any misalignment or other deviations from perfect positioning so that accuracy of the measurements is not lost. Further, any additional components for this purpose cannot add too much to the cost of the device in general. Also, variations in sample measurements conducted at different time periods, and those conducted using different instruments are common. A facile manner to deal with the variations is a dire need in the art.

SUMMARY OF THE INVENTION

In one aspect, the invention provides a method of calibrating a measurement device. The method comprises providing a Raman-active composition. The method then comprises impinging a light of a predetermined wavelength onto the Raman-active composition to provide an instant Raman scattering spectrum of the Raman-active composition.

In another aspect, the invention provides a measurement device that uses the method of the invention.

DETAILED DESCRIPTION OF THE INVENTION

As used herein and in the claims, the singular forms "a," "an," and "the" include the plural reference unless the context clearly indicates otherwise.

In one aspect, the invention provides a method for calibrating a measurement device. The method comprises providing a Raman-active composition. In some embodiments, the Raman-active composition is an organic compound that is active at a specific wavelength region. The wavelength region useful in the invention ranges from about 300 nanometers (nm) to about 1200 nm; in other embodiments, the wavelength region useful in the invention ranges from about 550 nm to about 800 nm; in further embodiments, the wavelength range useful in the invention ranges from about 550 nm to about 650 nm; and in yet other embodiments, the wavelength region useful in the invention ranges from about 650 nm to about 800 nm.

Raman scattering spectrum is known in the art, and is widely used in a variety of applications. Without being bound to any theory, Raman spectrum arises out of Raman effect, wherein a compound is excited by an incident radiation having a wavelength giving rise to an emission radiation, whose wavelength is different from the incident radiation. In one embodiment, the Raman-scattering spectrum useful in the invention comprises an emission radiation whose wavelength that ranges from about 650 nm to about 800 nm. Raman-active compositions that give rise to emission radiations that fall within a specified wavelength regions is known to those skilled in the art, and choice of such compositions can be appropriately.

The method of the invention includes recording an original Raman spectrum of a compound, which is to be used as a calibration standard. Subsequently, during use of the measurement device, an instant Raman spectrum of the calibration standard is obtained. Then, the instant Raman spectrum is compared with the original Raman spectrum to detect any differences, if any. Then, according to the extent of differences between the original Raman spectrum and the instant Raman spectrum, necessary correctional steps may be undertaken to produce instant Raman spectrum that is comparable within experimental limits to the original Raman spectrum. Such correctional steps will depend on the diagnosis of the problem leading to the difference and may include, for example, realigning or replacing the optics part of the device.

The organic compounds useful in the invention are those having Formula I:

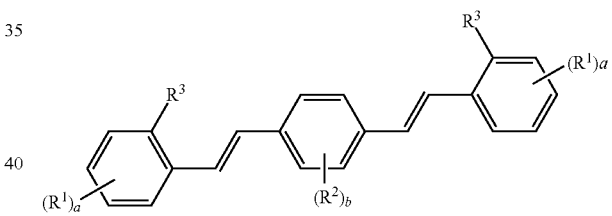

wherein $R^1$ and $R^2$ is at each instance a $C_1$-$C_{10}$ aliphatic, $C_6$-$C_{20}$ aromatic or a $C_6$-$C_{20}$ cycloaliphatic group; a and b are independently at each instance an integer ranging from 0 to 4; $R^3$ is a $C_1$-$C_{10}$ aliphatic group.

As used herein the term "aliphatic" refers to an organic group having a valence of at least one consisting of a linear or branched array of atoms which is not cyclic. Aliphatic groups are defined to comprise at least one carbon atom. Unsubstituted aliphatic groups include an array of atoms composed exclusively of carbon and hydrogen. Substituted aliphatic groups include an array of atoms comprising the aliphatic group and further include heteroatoms such as nitrogen, sulfur, silicon, selenium and oxygen or may be composed exclusively of carbon and hydrogen. Substituted aliphatic groups may further comprise a wide range of functional groups such as other aliphatic groups, alkenyl groups, alkynyl groups, halo aliphatic groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. As an illustration, methyl group would be $C_1$ aliphatic group, 2,2,5-trimethyl pentyl group would be a $C_8$ aliphatic group, 1,1,1-trichloro ethyl group would be a $C_2$ aliphatic group.

As used herein, the term "aromatic" includes but is not limited to groups having a cyclic structure with 4n+2 delocalized electrons, where n is an integer greater than or equal to 1. Some exemplary aromatic groups include, for example, phenyl, pyridyl, furanyl, thienyl, naphthyl, phenylene, and biphenyl groups. The aromatic group may further comprise nonaromatic components. Unsubstituted aromatic groups include an array of atoms that form part of the delocalized structure. Substituted aromatic groups may further comprise a wide range of functional groups that do not form part of the main delocalized structure, and may include groups such as aliphatic groups, alkenyl groups, alkynyl groups, haloaliphatic groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. As an illustration, the benzyl group is a $C_7$ aromatic group. Similarly, 2,4,6-trimethylphenyl group is a $C_9$ aromatic group. Further, a thiazole group would be a $C_3$ aromatic group.

As used herein the term "cycloaliphatic" refers to a radical having a valence of at least one, and comprising an array of atoms which is cyclic but which is not aromatic. A cycloaliphatic group may comprise one or more noncyclic components. Unsubstituted cycloaliphatic groups include an array of atoms composed exclusively of carbon and hydrogen. Substituted cycloaliphatic groups include an array of atoms comprising the cycloaliphatic group and further include heteroatoms such as nitrogen, sulfur, silicon, selenium and oxygen or may be composed exclusively of carbon and hydrogen. Substituted cycloaliphatic groups may further comprise a wide range of functional groups such as aliphatic groups, alkenyl groups, other alkynyl groups, halo aliphatic groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. As an illustration, a cyclohexyl group is a $C_6$ cycloaliphatic group, a methylcyclohexyl group is a $C_7$ cycloaliphatic group, and an adamantyl group is a $C_{10}$ cycloaliphatic group.

Organic compounds having Formula I useful in the invention may be commercially available from a variety of sources, such as Aldrich Chemical Company, Milwaukee, Wis., USA. Alternately, the compounds having Formula I may be synthesized using techniques known to those of ordinary skill in the art. The use of such a compound provides the advantage of being stable at a wide range of temperatures and over time. Thus, it is very useful as a fluorescent standard, and can be advantageously used in fluorescent measurement devices.

In one exemplary embodiment, an organic compound having formula II is used as the calibration standards:

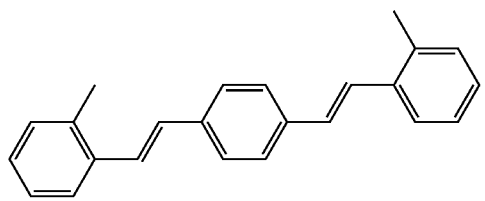

Formula II

In another aspect, the invention provides a measurement device that comprises the Raman-active composition. The measurement device comprises a movable light source that is capable of impinging a light beam having a predetermined wavelength onto the Raman-active composition. The device further comprises a detector that is capable of detecting an instant Raman spectrum from the active composition. The instant Raman spectrum is compared to an original Raman spectrum using a processor module.

The Raman-active compositions of the invention may be advantageously provided with each individual sample or a group of samples to be measured using the measurement device of the invention. By choosing a particular Raman-active composition whose excitation wavelength matches that of the wavelength being used for measurement, calibration can be effectively conducted in a single scanning sweep. Further, by providing the Raman-active composition with every sample, variations with samples and variations between instruments may be effectively countered. The variations that may arise from a variety of sources, and may include for example, variations in the power of the light source, gain of the detectors and detecting processes, such as use of amplifiers etc., which can be effectively neutralized by the use of the Raman-active compositions with each sample.

To implement a calibration step during the use of the device, an incident radiation from a light source is directed onto the Raman-active composition, as well as onto the sample to be measured. Since the Raman-scatter signal from the Raman-active composition maintains a constant separation from the excitation frequency based on the Raman scattering effect, it can serve as a stable control for normalizing the sample data generated from the measurement device. For example, if the emitted scatter signal is known to be X and at the time of measurement it is Y, then the ratio of X/Y can be used as a correction factor to neutralize any instrumental variations, such as in the laser power and the gain of the photodetectors. The use of such a standard eliminates the need to carefully tune each measurement device and at the same time provides the opportunity to compare results across multiple instruments.

Because the Raman scattering effect is stable (i.e. no photo-bleaching occurs), it can serve as a stable control to normalize the sample data generated by the measurement device, thereby eliminating the need to tune the device allowing a comparison of results across multiple instruments.

Thus, in another aspect, the invention provides a system that comprises the device of the invention. In a further aspect, the invention provides an assay measurement system that comprises the device of the invention. The assay measurement system may include, for example, an enzymatic assay system, an immunoassay measurement system, a sandwich immunoassay measurement system, a competitive immunoassay measurement system, and the like, and so on.

While only certain features of the invention have been illustrated and described herein, many modifications and changes will occur to those skilled in the art. It is, therefore, to be understood that the appended claims are intended to cover all such modifications and changes as fall within the true spirit of the invention.

I claim:
1. A method of calibrating a measurement device, said method comprising:
providing a Raman-active composition; and
impinging a light of a predetermined wavelength onto the Raman-active composition to provide an instant Raman scattering spectrum of the Raman-active composition,
wherein the Raman-active composition is a compound having Formula I

Formula I

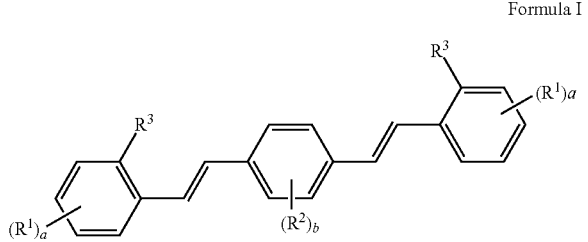

wherein $R^1$ and $R^2$ is at each instance a $C_1$-$C_{10}$ aliphatic, $C_6$-$C_{20}$ aromatic or a $C_6$-$C_{20}$ cycloaliphatic group; a and b are independently at each instance an integer ranging from 0 to 4; $R^3$ is a $C_1$-$C_{10}$ aliphatic group.

2. The method of the claim 1, wherein the calibrating further comprises comparing the instant Raman scattering spectrum with an original Raman scattering spectrum of the Raman-active composition.

3. The method of claim 1, wherein the Raman-active composition has a light absorption region ranging from about 300 nanometers to about 1200 nanometers.

4. The method of claim 1, wherein the instant Raman scattering spectrum is in a wavelength region ranging from about 650 nanometers to about 800 nanometers.

5. The method of claim 1, wherein the Raman-active composition is a compound having Formula II Formula II

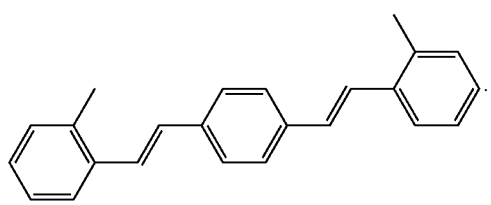

6. The method of claim 1, wherein the measurement device is a fluorescent measurement device.

7. A device that uses the method of claim 1.

8. A system that comprises the device of claim 7.

9. A measurement device comprising:
a Raman-active composition;
a movable light source that is capable of impinging a light beam having a predetermined wavelength onto the Raman-active composition;
a detector for detecting an instant Raman spectrum from the Raman-active composition; and
a processor module to compare the instant Raman scattering spectrum with an original Raman scattering spectrum of the Raman-active composition,
wherein the Raman-active composition is a compound having Formula I Formula I

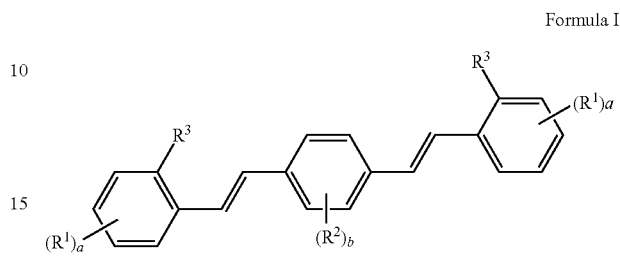

wherein $R^1$ and $R^2$ is at each instance a $C_1$-$C_{10}$ aliphatic, $C_6$-$C_{20}$ aromatic or a $C_6$-$C_{20}$ cycloaliphatic group; a and b are independently at each instance an integer ranging from 0 to 4; $R^3$ is a $C_1$-$C_{10}$ aliphatic group.

10. The measurement device of claim 9, wherein the wavelength ranges from about 300 nanometers to about 1200 nanometers.

11. The measurement device of claim 9, wherein the instant Raman scattering spectrum is in a wavelength region ranging from about 650 nanometers to about 800 nanometers.

12. The measurement device of claim 9, wherein the Raman-active composition is a compound having Formula II Formula II

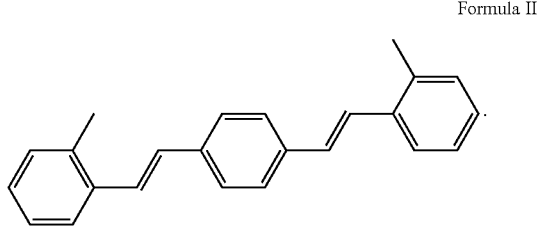 [SMILES: Cc1ccccc1/C=C/c1ccc(/C=C/c2ccccc2C)cc1]

13. A system that comprises the measurement device of claim 9.

14. An assay measurement system that comprises the measurement device of claim 9.

15. An immunoassay measurement system that comprises the measurement device of claim 9.

* * * * *